United States Patent
Goel et al.

(10) Patent No.: US 9,096,539 B2
(45) Date of Patent: Aug. 4, 2015

(54) SUBSTITUTED 4,5-DIHYDRO-2H-BENZO[E]INDAZOLE-9-CARBOXYLATES FOR THE TREATMENT OF DIABETES AND RELATED DISORDERS

(71) Applicant: Council of Scientific & Industrial Research, New Delhi (IN)

(72) Inventors: Atul Goel, Lucknow (IN); Gaurav Taneja, Lucknow (IN); Neha Rahuja, Lucknow (IN); Arun Kumar Rawat, Lucknow (IN); Natasha Jaiswal, Lucknow (IN); Akhilesh Kumar Tamrakar, Lucknow (IN); Arvind Kumar Srivastava, Lucknow (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/376,097

(22) PCT Filed: Jan. 29, 2013

(86) PCT No.: PCT/IN2013/000056
§ 371 (c)(1),
(2) Date: Jul. 31, 2014

(87) PCT Pub. No.: WO2013/114403
PCT Pub. Date: Aug. 8, 2013

(65) Prior Publication Data
US 2015/0005357 A1    Jan. 1, 2015

(30) Foreign Application Priority Data
Jan. 31, 2012  (IN) .............................. 262/DEL/2012

(51) Int. Cl.
*A61K 31/416*    (2006.01)
*C07D 487/00*    (2006.01)
*C07D 231/54*    (2006.01)
*C07D 409/04*    (2006.01)

(52) U.S. Cl.
CPC ............ *C07D 231/54* (2013.01); *A61K 31/416* (2013.01); *C07D 409/04* (2013.01)

(58) Field of Classification Search
CPC ........................... A61K 31/416; C07D 487/00
See application file for complete search history.

(56) References Cited

U.S. PATENT DOCUMENTS
2008/0234327 A1    9/2008    Cadieux et al.

FOREIGN PATENT DOCUMENTS
CN    101076332 A    11/2007
WO    2006080406 A1    8/2006

OTHER PUBLICATIONS

International Preliminary Report on Patentability Application No. PCT/IN2013/000056 Completed: May 5, 2014 11 pages.
International Search Report and Written Opinion of the International Searching Authority Application No. PCT/IN2013/000056 Completed: Apr. 11, 2013; Mailing Date: Apr. 19, 2013 8 pages.

*Primary Examiner* — Samantha Shterengarts
(74) *Attorney, Agent, or Firm* — St. Onge Steward Johnston & Reens, LLC (57) ABSTRACT

The present invention relates to the development of novel substituted 4,5-dihydro-2H-benzo[e]indazole-9-carboxylates, which can be used as therapeutic agents for the treatment and prevention of metabolic disorders, and a process of preparing said novel compounds. More particularly, the present invention relates to substituted 4,5-dihydro-2H-benzo[e]indazole-9-carboxylates and their related compounds, processes for preparing the said compounds and to their use in the treatment of diabetes and related metabolic disorders.

14 Claims, 3 Drawing Sheets

General Formula I

SUBSTITUTED 4,5-DIHYDRO-2H-BENZO[E]INDAZOLE-9-CARBOXYLATES FOR THE TREATMENT OF DIABETES AND RELATED DISORDERS

FIELD OF THE INVENTION

The present invention relates to the development of novel substituted 4,5-dihydro-2H-benzo[e]indazole-9-carboxylates, which can be used as therapeutic agents for the treatment and prevention of metabolic disorders, and a process of preparing said novel compounds. More particularly, the present invention relates to substituted 4,5-dihydro-2H-benzo[e]indazole-9-carboxylates and their related compounds, processes for preparing the said compounds and to their use in the treatment of diabetes and related metabolic disorders.

BACKGROUND OF THE INVENTION

Health and disease are coeval with life. A disease of all age group practically in all parts of the world, the Diabetes mellitus (Madhumeha). Diabetes mellitus is a chronic, incurable disease which altered the metabolism of lipids, carbohydrates and proteins, it is one of the common endocrine disorders with increased risk of complications from artery diseases, myocardial infarction, hypertension, and dyslipidemia, and clinically characterized by peripheral hyperglycemia. Diabetes can be classified clinically as insulin-dependent diabetes mellitus (IDDM, or type-1 diabetes) and non-insulin-dependent diabetes mellitus (NIDDM, or type-2 diabetes). Type-2 diabetes is common and found in >90% patient characterized by either normal/abnormal insulin secretion or function. It is considered a "modern day epidemic" and is rightly recognized as a global public health issue. The remedies available in modern system of medicine for the treatment of diabetic patients have been focused on dietary management of obesity and to improve insulin sensitivity, Sulfonylurea to enhance insulin secretion, metformin to inhibit hepatic glucose output, and acarbose to inhibit or reduce the rate of glucose absorption from the gut. Although treatment with highly active thiazolidinedione (TZD) class of drugs has significantly improved the clinical situation, but suffers with adverse side effects of hepatotoxicity, weight gain, edema and high rates of secondary failure. Current therapies to prevent diabetes mellitus (T2DM) have not kept pace with the disease's progression. The alarming situation emphasized the need to explore, evaluate and identify some new synthetic molecules with antidiabetic property have become one of the major objectives of present day diabetic research.

OBJECT OF THE INVENTION

The main object of the present invention is to provide substituted 4,5-dihydro-2H-benzo[e]indazole-9-carboxylates and related compounds for the treatment of diabetes and related disorders.

Another object of the present invention is to obtain/prepare therapeutically effective compound pharmaceutically acceptable formulations/delivery systems such as tablets, capsules, suppository, beads, aerosols, etc. for the treatment and prevention of diabetes and other related metabolic disorders.

Still another object of the present invention relates to the synthesis of the compounds which requires easily accessible precursors and mild reaction conditions in a single step at room temperature.

SUMMARY OF THE INVENTION

Accordingly the present invention provides Substituted 4,5-dihydro-2H-benzo[e]indazole-9-carboxylates having the general formula I, pharmaceutically acceptable salts and derivatives thereof General Formula I (a) wherein $R^1$ is independently selected from the groups consisting of optionally substituted aryl, optionally substituted heteroaryl;
(b) wherein $R^2$, $R^3$ are independently selected from the groups consisting of hydrogen, optionally substituted alkyl, optionally substituted aryl, optionally substituted heteroaryl, optionally substituted cycloalkenyl;
(c) wherein $R^4$ is independently selected from the groups consisting of optionally substituted alkylthio, optionally substituted alkylsulfonyl, optionally substituted amines;
(d) wherein R is independently selected from the groups consisting of hydrogen, optionally substituted alkyl, optionally substituted alkenyl, optionally substituted aryl groups;
(e) wherein Y is selected from the groups consisting of one methylene group, two methylene groups, or optionally substituted methylene group;

In an embodiment of the invention wherein the representative compounds of the general formula I are;

i. Methyl 6-(4-bromophenyl)-8-(methylthio)-2-phenyl-4,5-dihydro-2H-benzo[e]indazole-9-carboxylate (1)
ii. Methyl 6-(4-chlorophenyl)-8-(methylthio)-2-phenyl-4,5-dihydro-2H-benzo[e]indazole-9-carboxylate (2)
iii. Methyl 6-(4-methoxyphenyl)-8-(methylthio)-2-phenyl-4,5-dihydro-2H-benzo[e]indazole-9-carboxylate (3)
iv. Methyl 8-(methylthio)-2,6-diphenyl-4,5-dihydro-2H-benzo[e]indazole-9-carboxylate (4)
v. Methyl 8-(methylthio)-2-phenyl-6-p-tolyl-4,5-dihydro-2H-benzo[e]indazole-9-carboxylate (5)
vi. Methyl 8-(methylthio)-6-(naphthalen-1-yl)-2-phenyl-4,5-dihydro-2H-benzo[e]indazole-9-carboxylate (6)
vii. Methyl 8-(methylthio)-2-phenyl-6-(thiophen-2-yl)-4,5-dihydro-2H-benzo[e]indazole-9-carboxylate (7)
viii. methyl 6-(4-fluorophenyl)-8-(methylthio)-2-phenyl-4,5-dihydro-2H-benzo[e]indazole-9-carboxylate (8)
ix. methyl 8-(methylthio)-2-phenyl-6-(pyren-1-yl)-4,5-dihydro-2H-benzo[e]indazole-9-carboxylate (9)
x. methyl 6-(4-fluorophenyl)-8-(methylsulfonyl)-2-phenyl-4,5-dihydro-2H-benzo[e]indazole-9-carboxylate (10)
xi. methyl 8-(methylsulfonyl)-6-(naphthalen-1-yl)-2-phenyl-4,5-dihydro-2H-benzo[e]indazole-9-carboxylate (11)
xii. methyl 8-(methylsulfonyl)-2-phenyl-6-(p-tolyl)-4,5-dihydro-2H-benzo[e]indazole-9-carboxylate (12)

xiii. Methyl 5-(methylthio)-7-(naphthalen-2-yl)-2-phenyl-2,8-dihydroindeno[2,1-c]pyrazole-4-carboxylate (13)

In an embodiment of the invention wherein the compounds are useful for the treatment of diabetes and related disorders.

In another embodiment of the invention wherein the compounds showed PTB-1B inhibition with $IC_{50}$ of 7-8 μM.

In still another embodiment of the invention wherein the compounds showed decrease in the blood glucose level at 2 hrs in the test group compared with that of the control was 35.8% and 23.5% whereas the decrease in the Januvia treated group was 35.0%. In still anoher embodiment of the present invention also provides a process for the synthesis of 4,5-dihydro-2H-benzo[e]indazole-9-carboxylates having the general formula I, which comprises;

step (a) reacting 2H-pyran-2-ones with a cyclic ketone in presence of an alkali base for a period upto 24 hours at a temperature ranging between 0 to 50 degree centigrade;

step (b) pouring the reaction mixture to an ice cold water and neutralized with an acid;

step (c) purifying the product by chromatographic method, step (d) reacting the compound obtained in above step with m-chloroperbenzoic acid in dichloromethane at a temperature ranging between 25 to 28 degree C. for a period ranging between 1-2 hrs, treating the reaction mixture with sodium bicarbonate solution to obtain the desired compound.

In an embodiment of the invention wherein substituted 2H-pyran-2-ones is used to react with substituted or unsubstituted cyclic ketones such as 2-phenyl-6,7-dihydro-2H-indazol-4(5H)-one as described in examples 1-13.

In another embodiment of the invention wherein the organic solvent used is selected from the group consisting of acetone, N,N-dimethyl formamide, N,N-dimethyl acetamide, dimethyl sulfoxide, benzene, toluene, xylene, chlorobenzene, tetrahydrofuran.

In one more embodiment of the invention base used is selected from a group consisting of NaOH, KOH, NaH, t-BuOK, $K_2CO_3$, and NaOEt, In still another embodiment of the invention wherein the neutralization of the resultant compounds is effected by acidifying the reaction mixture with dilute hydrochloric acid, sulfuric acid, acetic acid A pharmaceutical, composition comprising an effective amount of compound of formula I optionally along with pharmaceutically acceptable, excipients, carrier/s, lubricants, and diluents.

The effective amount of the compound in the composition is ranging 10 mg to 500 mg.

The pharmaceutically acceptable excipient may be selected from the group consisting of starch, lactose, cellulose.

The diluents used may be selected from the group consisting of starch, lactose, dicalcium phosphate.

The lubricant may be selected from the group comprising of talc, magnesium stearate.

A method of treating diabetes in a subject, wherein the said method comprising the step of administering to the subject suffering from diabeties, a pharmaceutical composition an effective amount of compound of formula I optionally along with pharmaceutically acceptable, excipients, carrier/s, lubricants, diluents.

BRIEF DESCRIPTION OF THE DRAWINGS

The present invention may be more clearly understood by reference to the following Sheets.

DETAILED DESCRIPTION OF THE INVENTION

Accordingly, the present invention provides a compound of formula I:

General formula I

Wherein $R^1$ is independently selected from the groups consisting of optionally substituted aryl, optionally substituted heteroaryl;

Wherein $R^2$, $R^3$ are independently selected from the groups consisting of hydrogen, optionally substituted alkyl, optionally substituted aryl, optionally substituted heteroaryl, optionally substituted cycloalkenyl, Wherein $R^4$ is independently selected from the groups consisting of optionally substituted alkylthio, optionally substituted alkylsulfonyl, optionally substituted amines etc, Wherein R is independently selected from the groups consisting of hydrogen, optionally substituted alkyl, optionally substituted alkenyl, optionally substituted aryl groups Wherein Y is selected from the groups consisting of one methylene group, two methylene groups, or optionally substituted methylene group.

Among a large number of the molecules having the formula (I) incorporating substituted 4,5-dihydro-2H-benzo[e]indazole-9-carboxylates and their related compounds and their use in the treatment of diabetes and related disorders and related compounds shown in examples 1 to 13 and in the drawing accompanying the specification.

Figure 1:
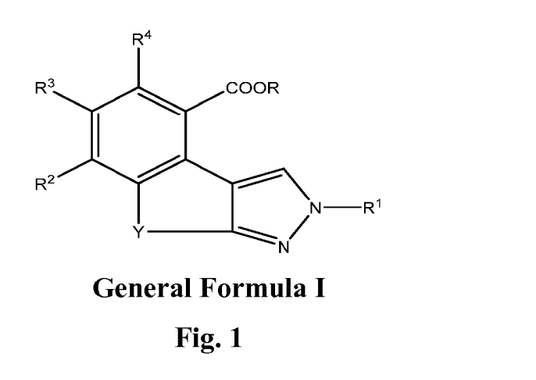
FIG. 1 illustrates the general formula I for the novel 4,5-dihydro-2H-benzo[e]indazole-9-carboxylates compounds of the invention.
Figure 1A:
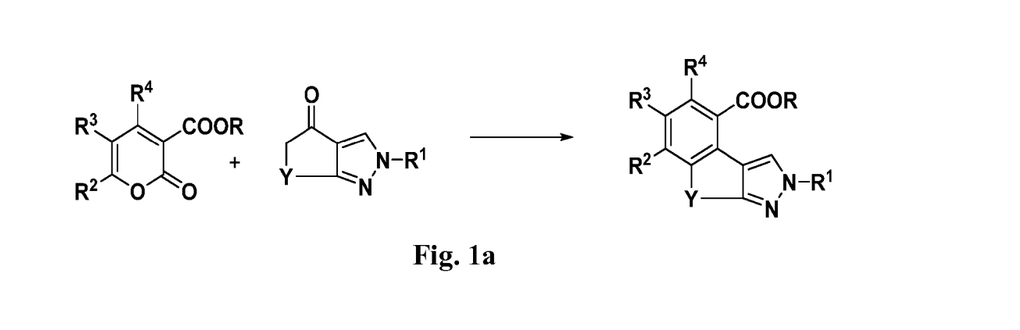
FIG. 1a illustrates the reaction sequence resulting in the preparation of various 4,5-dihydro-2H-benzo[e]indazole derivatives and related compounds.

FIG. 1a represents a preferred embodiment of this process for the compounds having the formula (I)

The starting material 2H-pyran-2-ones are known and has been prepared by the reaction of methyl 2-cyano/methoxycarbonyl-3,3-dgmethylsulfanyl)acrylate with substituted acetophenones under alkaline conditions in dry DMSO in high yields. The 2H-pyran-2-ones is treated with cyclic ketone preferably dissolved either in a volatile solvents such as acetone, THF or in a high boiling solvents such as dimethyl formamide, dimethyl acetamide, dimethyl sulfoxide in presence of an alkali such as K₂CO₃, KOH, t-BuOK, NaH. Preferably equimolar amounts of the reagents are used and the reaction takes place within a period of 24 hours at the reaction temperature between 25-50° C. and purifying the final product by chromatographic method.

Materials and Method—

Drugs and Chemicals—

Streptozotocin a most widely used chemical diabetogen was procured from Sigma-Aldrich chemicals Co., St Louis, Mo., USA. All the chemicals and reagents used were obtained from local sources and were of analytical grade.

Chemistry:

Synthesis of the Compounds Using Various Reaction Conditions:

The synthesis of the compounds of the invention was achieved as shown in FIG. 1a. The reaction conditions were optimized for EXAMPLE 1 by reacting a mixture of methyl 6-(4-bromophenyl)-4-(methylthio)-2-oxo-2H-pyran-3-carboxylate (353 mg, 1 mmol) and 2-phenyl-6,7-dihydro-2H-indazol-4(5H)-one (212 mg, 1 mmol) in the presence of different bases and solvents as mentioned in Table below:

TABLE

| Entry | Base | Solvent | Temp | Duration | Yield[c] (%) |
|---|---|---|---|---|---|
| 1 | KOH[a] | DMF | 25° C. | 6 h | 63 |
| 2 | KOH[a] | DMF | 60° C. | 24 h | 35 |
| 3 | KOH[a] | DMF | 100° C. | 24 h | 15 |
| 3 | KOH[a] | DMSO | 25° C. | 10 h | 18 |
| 4 | NaH[b] | THF | 25° C. | 5 h | traces |
| 5 | NaH[b] | DMF | 25° C. | 3 h | 20 |
| 6 | t-BuOK[b] | THF | 25° C. | 15 h | traces |

[a]1.2 Equivalent of base was used in the reactions.
[b]2 Equivalent of base was used in the reactions.
[c]Isolated yield.

Following examples are given by way of illustration and should not construed the scope of the present inventions.

Example 1

Synthesis of methyl methyl 6-(4-bromophenyl)-8-(methylthio)-2-phenyl-4,5-dihydro-2H-benzo[e]indazole-9-carboxylate (1)

A mixture of methyl 6-(4-bromophenyl)-4-(methylthio)-2-oxo-2H-pyran-3-carboxylate (353 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 6 hr. At the end the reaction mixture was poured into ice water with vigorous stirring and finally neutralized with dilute HCl. The solid thus obtained was filtered and purified on a neutral alumina column using 15% chloroform in hexane as eluent to yield 317 mg (63%) of methyl 6-(4-bromophenyl)-8-(methylthio)-2-phenyl-4,5-dihydro-2H-benzo[e]indazole-9-carboxylate.

White solid; mp-164-166° C.; ¹H NMR (300 MHz, CDCl₃) δ 2.48 (s, 3H, CH₃), 2.85 (s, 4H, 2CH₂), 4.01 (s, 3H, OCH₃), 7.10-7.34 (m, 4H, ArH), 7.40-7.53 (m, 2H, ArH), 7.54-7.72 (m, 4H, ArH), 7.98 (s, 1H, ArH); ¹³C NMR (75.5 MHz); δ 18.83, 22.11, 27.75, 53.29, 117.11, 119.40, 122.23, 123.51, 126.88, 128.29, 129.07, 129.90, 131.18, 132.00, 132.38, 133.47, 140.12, 140.41, 142.68, 153.14, 170.42; IR (KBr) 1725.9 cm⁻¹ (CO); MS (ESI) m/z 506 (M⁺+1);

Example 2

Synthesis of methyl 6-(4-chlorophenyl)-8-(methylthio)-2-phenyl-4,5-dihydro-2H-benzo[e]indazole-9-carboxylate (2)

A mixture of methyl 6-(4-chlorophenyl)-4-(methylthio)-2-oxo-2H-pyran-3-carboxylate (330 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 6 hr. At the end the reaction mixture was poured into ice water with vigorous stirring and finally neutralized with dilute HCl. The solid thus obtained was filtered and purified on a neutral alumina column using 15% chloroform in hexane as eluent to yield 267 mg (58%) of methyl 6-(4-chlorophenyl)-8-(methylthio)-2-phenyl-4,5-dihydro-2H-benzo[e]indazole-9-carboxylate.

White solid; mp-159-162° C.; ¹H NMR (300 MHz, CDCl₃) δ 2.50 (s, 3H, SCH₃), 2.87 (s, 4H, 2CH₂), 4.02 (s, 3H, OCH₃), 7.12-7.39 (m, 4H, ArH), 7.39-7.59 (m, 4H, ArH), 7.63-7.79 (m, 2H, ArH, J=9.0 Hz), 8.00 (s, 1H, ArH); ¹³C NMR (200 MHz); δ 18.81, 22.10, 27.78, 53.27, 114.48, 117.14, 119.48, 123.50, 126.89, 128.24, 129.07, 129.08, 130.01, 130.90, 132.46, 133.45, 134.13, 139.66, 140.39, 142.73, 153.16, 170.75; IR (KBr) 1723.3 cm⁻¹ (CO); MS (ESI) m/z 461 (M++1).

Example 3

Synthesis of methyl 6-(4-methoxyphenyl)-8-(methylthio)-2-phenyl-4,5-dihydro-2H-benzo[e]indazole-9-carboxylate (3)

A mixture of methyl 6-(4-methoxyphenyl)-4-(methylthio)-2-oxo-2H-pyran-3-carboxylate (306 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 8 hr. At the end the reaction mixture was poured into ice water with vigorous stirring and finally neutralized with dilute HCl. The solid thus obtained was filtered and purified on a neutral alumina column using 15% chloroform in hexane as eluent to yield 269 mg (59%) of methyl 6-(4-methoxyphenyl)-8-(methylthio)-2-phenyl-4,5-dihydro-2H-benzo[e]indazole-9-carboxylate.

White solid; mp-172-174° C.; $^1$H NMR (300 MHz, CDCl$_3$) d 2.49 (s, 3H, CH$_3$), 2.72-2.96 (m, 4H, 2CH$_2$), 3.88 (s, 3H, OCH$_3$), 4.01 (s, 3H, OCH$_3$), 6.94-7.05 (m, 2H, ArH), 7.16-7.36 (m, 4H, ArH), 7.40-7.53 (m, 2H, ArH), 7.62-7.73 (m, 2H, ArH), 7.98 (s, 1H, ArH); IR (KBr) 1722.2 cm$^{-1}$ (CO); MS (ESI) m/z 457 (M++1).

Example 4

Synthesis of methyl 8-(methylthio)-2,6-diphenyl-4,5-dihydro-2H-benzo[e]indazole-9-carboxylate (4)

A mixture of methyl 4-(methylthio)-2-oxo-6-phenyl-2H-pyran-3-carboxylate (276 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 7 hr. At the end the reaction mixture was poured into ice water with vigorous stirring and finally neutralized with dilute HCl. The solid thus obtained was filtered and purified on a neutral alumina column using 15% chloroform in hexane as eluent to yield 234 mg (55%) of methyl 8-(methylthio)-2,6-diphenyl-4,5-dihydro-2H-benzo[e]indazole-9-carboxylate.

White solid; mp-173-175° C. $^1$H NMR (300 MHz, CDCl$_3$) d 2.48 (s, 3H, CH$_3$), 2.80-2.86 (m, 2H, CH$_2$), 2.86-2.95 (m, 2H, CH$_2$), 4.01 (s, 3H, OCH$_3$), 7.19 (m, 1H, ArH), 7.24-7.35 (m, 3H, ArH), 7.36-7.50 (m, 5H, ArH), 7.64-7.69 (m, 2H, ArH), 7.98 (s, 1H, ArH); $^{13}$C NMR (75.5 MHz); d 18.79, 22.16, 27.75, 53.37, 117.24, 119.37, 123.45, 126.82, 127.97, 128.03, 128.77, 129.26, 129.48, 129.97, 132.49, 133.20, 140.38, 141.31, 143.93, 153.37, 170.66; IR (KBr) 1726 cm$^{-1}$ (CO); MS (ESI) m/z 427 (M$^+$+1);

Example 5

Synthesis of methyl 8-(methylthio)-2-phenyl-6-p-tolyl-4,5-dihydro-2H-benzo[e]indazole-9-carboxylate (5)

A mixture of methyl 4-(methylthio)-2-oxo-6-p-tolyl-2H-pyran-3-carboxylate (290 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 7 hr. At the end the reaction mixture was poured into ice water with vigorous stirring and finally neutralized with dilute HCl. The solid thus obtained was filtered and purified on a neutral alumina column using 15% chloroform in hexane as eluent to yield 334 mg (74%) of methyl 8-(methylthio)-2-phenyl-6-p-tolyl-4,5-dihydro-2H-benzo[e]indazole-9-carboxylate.

White solid; mp-178-180° C.; $^1$H NMR (300 MHz, CDCl$_3$) d 2.43 (s, 3H, CH$_3$), 2.48 (s, 3H, CH$_3$), 2.78-3.00 (m, 4H, 2CH$_2$), 4.01 (s, 3H, OCH$_3$), 7.18 (m, 1H, ArH), 7.24-7.35 (m, 5H, ArH), 7.40-7.53 (m, 2H, ArH), 7.63-7.72 (m, 2H, ArH), 7.98 (s, 1H, ArH); $^{13}$C NMR (75.5 MHz); d 18.79, 21.62, 22.14, 27.75, 53.24, 117.29, 119.38, 123.38, 126.76, 128.00, 129.36, 129.44, 129.88, 130.75, 132.56, 133.08, 137.74, 138.33, 140.43, 143.92, 153.32, 170.61; IR (KBr) 1718.1 cm$^{-1}$ (CO); MS (ESI) m/z 441 (M$^+$+1); HRMS (EI) calculated mass for C$_{27}$H$_{24}$N$_2$O$_2$S: 440.1559. found 440.1547.

Example 6

Synthesis of methyl 8-(methylthio)-6-(naphthalen-1-yl)-2-phenyl-4,5-dihydro-2H-benzo[e]indazole-9-carboxylate (6)

A mixture of methyl 4-(methylthio)-6-(naphthalen-1-yl)-2-oxo-2H-pyran-3-carboxylate (326 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 8 hr. At the end the reaction mixture was poured into ice water with vigorous stifling and finally neutralized with dilute HCl. The solid thus obtained was filtered and purified on a neutral alumina column using 15% chloroform in hexane as eluent to yield 228 mg (48%) of methyl 8-(methylthio)-6-(naphthalen-1-yl)-2-phenyl-4,5-dihydro-2H-benzo[e]indazole-9-carboxylate.

White solid; mp-182-184° C.; ¹H NMR (300 MHz, CDCl₃) d 2.46 (s, 3H, CH₃), 2.53-2.65 (m, 2H, CH₂), 2.69-2.81 (m, 2H, CH₂), 4.06 (s, 3H, OCH₃), 7.21 (s, 1H, ArH), 7.26 (s, 1H, ArH), 7.28-7.58 (m, 7H, ArH), 7.64-7.69 (m, 1H, ArH), 7.69-7.71 (m, 1H, ArH), 7.89-7.98 (m, 2H, ArH), 8.01 (s, 1H, ArH); ¹³C NMR (75.5 MHz); d 18.48, 22.06, 27.61, 53.39, 119.46, 123.43, 125.82, 126.22, 126.52, 126.88, 126.99, 128.54, 128.80, 129.22, 129.93, 133.67, 133.88, 138.90, 153.32, 170.69; IR (KBr) 1726.1 cm⁻¹ (CO); MS (ESI) m/z 477 (M⁺+1).

Example 7

Synthesis of methyl 8-(methylthio)-2-phenyl-6-(thiophen-2-yl)-4,5-dihydro-2H-benzo[e]indazole-9-carboxylate (7)

A mixture of methyl 4-(methylthio)-2-oxo-6-(thiophen-2-yl)-2H-pyran-3-carboxylate (282 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 6 hr. At the end the reaction mixture was poured into ice water with vigorous stirring and finally neutralized with dilute HCl. The solid thus obtained was filtered and purified on a neutral alumina column using 15% chloroform in hexane as eluent to yield 211 mg of (49%) of methyl 8-(methylthio)-2-phenyl-6-(thiophen-2-yl)-4,5-dihydro-2H-benzo[e]indazole-9-carboxylate.

White solid; mp-174-176° C.; ¹H NMR (300 MHz, CDCl₃) d 2.49 (s, 3H, CH₃), 2.82-2.96 (s, 2H, CH₂), 3.02-3.16 (m, 2H, CH₂), 4.00 (s, 3H, OCH₃), 7.02-7.18 (m, 2H, ArH), 7.28-7.53 (m, 5H, ArH), 7.62-7.73 (m, 2H, ArH), 7.97 (s, 1H, ArH); ¹³C NMR (75.5 MHz); d 18.82, 22.08, 27.75, 53.28, 117.11, 119.43, 123.50, 126.37, 126.83, 127.64, 127.87, 128.33, 129.90, 130.26, 131.48, 133.34, 133.55, 136.34, 140.39, 141.90, 153.16, 170.36; IR (KBr) 1716.8 cm⁻¹ (CO); MS (ESI) m/z 433 (M⁺+1); HRMS (EI) calculated mass for C₂₄H₂₀N₂O₂S₂: 432.0966. found. 432.0970.

Example 8

Synthesis of methyl 6-(4-fluorophenyl)-8-(methylthio)-2-phenyl-4,5-dihydro-2H-benzo[e]indazole-9-carboxylate (8)

A mixture of methyl 4-(methylthio)-2-oxo-6-(4-fluorophenyl)-2H-pyran-3-carboxylate (294 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 7 hr. At the end the reaction mixture was poured into ice water with vigorous stirring and finally neutralized with dilute HCl. The solid thus obtained was filtered and purified on a neutral alumina column using 15% chloroform in hexane as eluent to yield 52% of methyl 6-(4-fluorophenyl)-8-(methylthio)-2-phenyl-4,5-dihydro-2H-benzo[e]indazole-9-carboxylate. White solid; mp-182-184° C.; ¹H NMR (300 MHz, CDCl₃) δ 2.48 (s, 3H, CH₃), 2.82-2.90 (m, 4H, 2CH₂), 4.01 (s, 3H, OCH₃), 7.10-7.19 (m, 3H, ArH), 7.27-7.36 (m, 3H, ArH), 7.42-7.51 (m, 2H, ArH), 7.67 (d, J=7.62 Hz, 2H, ArH), 7.98 (s, 1H, ArH); MS (ESI) m/z 445 (M⁺+1).

Example 9

Synthesis of methyl 8-(methylthio)-2-phenyl-6-(pyren-1-yl)-4,5-dihydro-2H-benzo[e]indazole-9-carboxylate (9)

A mixture of methyl 4-(methylthio)-2-oxo-6-(pyren-1-yl)-2H-pyran-3-carboxylate (400 mg, 1 mmol), 2-phenyl-6,7-dihydro-2H-indazol-4(5H)-one (212 mg, 1 mmol) and powdered KOH (84 mg, 1.5 mmol) in dry DMF (5 mL) was stirred at 25° C. for 8 hr. At the end the reaction mixture was poured into ice water with vigorous stirring and finally neutralized with dilute HCl. The solid thus obtained was filtered and purified on a neutral alumina column using 15% chloroform in hexane as eluent to yield 58% of methyl 8-(methylthio)-2-phenyl-6-(pyren-1-yl)-4,5-dihydro-2H-benzo[e]indazole-9-carboxylate. Yellow solid; mp-174-176° C.; ¹H NMR (300 MHz, CDCl₃) δ 2.49 (s, 3H, CH₃), 2.60-2.67 (m, 2H, CH₂), 2.71-2.77 (m, 2H, CH₂), 4.08 (s, 3H, OCH₃), 7.27-7.36 (m, 2H, ArH), 7.47 (t, J₁=8.28 Hz, J₂=7.50 Hz, 2H, ArH), 7.65-7.72 (m, 2H, ArH), 7.73-7.81 (m, 1H, ArH), 7.90 (d, J=7.77

Hz, 1H, ArH), 7.99-8.09 (m, 3H, ArH), 8.14 (s, 2H, ArH), 8.18-8.29 (m, 3H, ArH); MS (ESI) m/z 551 (M⁺+1).

Example 10

Synthesis of methyl 6-(4-fluorophenyl)-8-(methylsulfonyl)-2-phenyl-4,5-dihydro-2H-benzo[e]indazole-9-carboxylate (10)

A mixture of methyl 6-(4-fluorophenyl)-8-(methylthio)-2-phenyl-4,5-dihydro-2H-benzo[e]indazole-9-carboxylate (44.4 mg, 0.1 mmol), m-chloroperbenzoic acid (85.5 mg, 0.5 mmol) in dichloromethane (5 mL) was stirred at 25° C. for 1 hr. At the end the reaction mixture was treated with saturated solution of sodium bicarbonate. The mixture was extracted with dichloromethane and organic layer was reduced under vacuum. The crude mixture was purified on a silicagel column using 40% chloroform in hexane as eluent to yield 78% of methyl 6-(4-fluorophenyl)-8-(methylsulfonyl)-2-phenyl-4,5-dihydro-2H-benzo[e]indazole-9-carboxylate. White solid; mp-245-247° C.; ¹H NMR (300 MHz, CDCl₃) δ 2.84-2.94 (m, 2H, CH₂), 2.95-3.06 (m, 2H, CH₂), 3.20 (s, 3H, SO₂CH₃), 4.03 (s, 3H, OCH₃), 7.12-7.22 (m, 2H, ArH), 7.27-7.35 (m, 3H, ArH), 7.44-7.52 (m, 2H, ArH), 7.64-7.70 (m, 2H, ArH), 7.78 (s, 1H, ArH), 8.02 (s, 1H, ArH); MS (ESI) m/z 477 (M⁺+1).

Example 11

Synthesis of methyl 8-(methylsulfonyl)-6-(naphthalen-1-yl)-2-phenyl-4,5-dihydro-2H-benzo[e]indazole-9-carboxylate (11)

A mixture of methyl 8-(methylthio)-6-(naphthalen-1-yl)-2-phenyl-4,5-dihydro-2H-benzo[e]indazole-9-carboxylate (47.6 mg, 0.1 mmol), m-chloroperbenzoic acid (85.5 mg, 0.5 mmol) in dichloromethane (5 mL) was stirred at 28° C. for 1.5 hr. At the end the reaction mixture was treated with saturated solution of sodium bicarbonate. The mixture was extracted with dichloromethane and organic layer was reduced under vacuum. The crude mixture was purified on a silicagel column using 40% chloroform in hexane as eluent to yield 80% of methyl 8-(methylsulfonyl)-6-(naphthalen-1-yl)-2-phenyl-4,5-dihydro-2H-benzo indazole-9-carboxylate.

White solid; mp-204-206° C.; ¹H NMR (300 MHz, CDCl₃) δ 2.70-2.98 (m, 3H), 3.05-3.18 (m, 1H), 3.24 (s, 3H, SO₂CH₃), 4.06 (s, 3H, OCH₃), 7.33-7.65 (m, 7H, ArH), 7.67-7.78 (m, 2H, ArH), 7.82-8.04 (m, 4H, ArH), 8.05-8.14 (m, 1H, ArH). MS (ESI) m/z 509 (M⁺+1).

Example 12

Synthesis of methyl 8-(methylsulfonyl)-2-phenyl-6-(p-tolyl)-4,5-dihydro-2H-benzo[e]indazole-9-carboxylate (12)

A mixture of methyl 8-(methylthio)-2-phenyl-6-p-tolyl-4,5-dihydro-2H-benzo[e]indazole-9-carboxylate (44.0 mg, 0.1 mmol), m-chloroperbenzoic acid (85.5 mg, 0.5 mmol) in dichloromethane (5 mL) was stirred at 28° C. for 2 hr. At the end the reaction mixture was treated with saturated solution of sodium bicarbonate. The mixture was extracted with dichloromethane and organic layer was reduced under vacuum. The crude mixture was purified on a silicagel column using 40% chloroform in hexane as eluent to yield 80% of methyl 8-(methylsulfonyl)-2-phenyl-6-(p-tolyl)-4,5-dihydro-2H-benzo[e]indazole-9-carboxylate.

White solid; mp-228-230° C.; ¹H NMR (300 MHz, CDCl₃) δ 2.43 (s, 3H, CH₃), 2.85-2.90 (m, 2H, CH₂), 3.00-3.08 (m, 2H, CH₂), 3.20 (s, 3H, SO₂CH₃), 4.03 (s, 3H, OCH₃), 7.19-7.38 (m, 5H, ArH), 7.44-7.54 (m, 2H, ArH), 7.64-7.74 (m, 2H, ArH), 7.77-7.86 (m, 1H, ArH), 7.79-8.07 (m, 1H, ArH), MS (ESI) m/z 473 (M⁺+1).

Example 13

Methyl 5-(methylthio)-7-(naphthalen-2-yl)-2-phenyl-2,8-dihydroindeno[2,1-c]pyrazole-4-carboxylate (13)

A mixture of methyl 4-(methylthio)-6-(naphthalen-2-yl)-2-oxo-2H-pyran-3-carboxylate (163 mg, 0.5 mmol, 1 equiv), 2-phenyl-5,6-dihydrocyclopenta[c]pyrazol-4(2H)-one (100 mg, 0.5 mmol, 1 equiv) and KOH (42 mg, 0.75 mmol, 1.5 equiv) in dry DMF (5 ml) was stirred at room temperature for 45 min. The progress of reaction was monitored by TLC, and on completion the reaction mixture was poured onto crushed ice with vigorous stirring and finally neutralized with 10% HCl. The precipitate obtained was filtered and purified on a silica gel column using 10% ethyl acetate in hexane as the eluent to afford the compound in 25% (58 mg) yield.

mp (n-hexane/ethyl acetate)=235-237° C.; MS (ESI) 463 [M+H$^+$]; IR (KBr) $\lambda$=1729 (CO) cm$^{-1}$; $^1$H NMR (300 MHz, CDCl$_3$) $\delta$=2.55 (s, 3H, SCH$_3$), 3.01-3.19 (m, 2H, CH$_2$), 4.13 (s, 3H, OCH$_3$), 7.05-7.45 (m, 3H, ArH), 7.45-7.81 (m, 8H, ArH), 7.93-8.10 (m, 2H, ArH), 8.13-8.23 (m, 1H, ArH) ppm;

Experimental Animals—

Male albino rats of Sprague Dawley strain of 8 to 10 weeks of age and 160±20 g of body weight were procured from the animal colony of the Institute. The work with these animals was cleared by institutional ethics committee for animal study and was conducted in accordance with the guidelines of the Committee for the purpose of Control and Supervision of Experiments on Animals (CPCSEA) formed by the Government of India in 1964. The institute has taken permission from the animal ethical committee for the work (No. 129/07/Biocmem/IAEC). The animals were housed four or five in a polypropylene cage in the animal house. The following norms were always followed for animal room environment: temperature 23±2° C.; humidity 50-60%; light 300 lux at floor level with regular 12 hr light cycle; noise level 50 decibel; ventilation 10-15 air changes per hour. After randomization into various groups, the rats were acclimatized for 2 to 3 days in the new environment before initiation of experiment. Standard pellets were used as a basal diet during the experimental period. The animals had free access to pellet diet and tap water unless stated otherwise.

In Vivo Antihyperglycemic Activity Evaluation

Preparation of Test Compounds and the Standard Antidiabetic Drug:

The test compounds and standard antidiabetic drug Januvia were prepared in 1.0% freshly prepared Gum acacia.

Assessment of Test Compounds for Antihyperglycaemic Activity on Sucrose Loaded Normoglycaemic Rats—

In order to search towards the antidiabetic activity, synthetic compounds were preliminary evaluated for their effect on glucose tolerance in normal rats. It is an indirect effect of measuring antihyperglycaemic activity. Male albino rats of Wistar strain of body weight 160±20 g were selected for this study. The blood glucose of each animal was checked by glucometer using glucostrips (Accu-check) after 16 hours starvation. Animals showing blood glucose between 60 to 80 mg/dl (3.33 to 4.44 mM) were divided into groups of five to six animals in each. Rats of experimental group were administered suspension of the desired test compound orally (made in 1.0% gum acacia). The standard dose decided for Synthetic compounds is 100 mg/kg body weight. Animals of control group were given an equal amount of 1.0% gum acacia. A sucrose load (10.0 g/kg) was given to each animal orally exactly after 30 min post administration of the test sample/vehicle. Blood glucose profile of each rat was again determined at 30, 60, 90 and 120 min post administration of sucrose by glucometer. Food but not water was withheld from the cages during the course of experimentation. Quantitative glucose tolerance of each animal was calculated by area under curve (AUC) method using Prism Software. Comparing the AUC of experimental and control groups determined the percentage antihyperglycaemic activity. Statistical comparison was made by Dunnett's test. Samples showing significant inhibition ($p<0.05$, $p<0.01$, $p<0.001$) on postprandial hyperglycemia (AUC) were considered as active samples.

Assessment of Test Compounds for Antihyperglycaemic Activity in Low Dosed Streptozotocin Induced Diabetic Rats—

Induction of Diabetes in Rats:

Overnight starved male albino rats of Sprague Dawley strain were used and Diabetes was induced in the animals by single intraperitoneal injection of Streptozotocin at 60 mg/kg body weight dose prepared in 0.1M citrate buffer (pH 4.5). Fasting blood glucose level was measured by using a Glucometer (ACCU-CHEK II; Roche Diagnostics, USA) after 48 hours and animals showing blood glucose level above 300 mg/di were considered as diabetic.

Grouping and Treatment:

The diabetic animals were divided into four groups (Group 1 to 4) each consisting 6 rats. Group 1 received 0.4 ml vehicle (1% gum acacia). Group 2 received the test compound 5 at an oral dose of 100 mg/kg/body weight. Group 3 was given compound 6 at an oral dose of 100 mg/kg/body weight. The standard antidiabetic drug Januvia was given to the animals of Group 4 at an oral dose of 50 mg/kg body weight. The blood glucose levels of each animal were again measured by glucostrips at 1 h, 2 h, 3 h, 4 h, 5 h and 24 h post treatment with the test sample/standard drug by glucometer. Food but not water was withheld from the cages during the course of experimentation. Percent hyperglycemic activity was determined by comparing the AUC (area under curve) of experimental groups with that of the vehicle treated control group.

Assessment of Test Compounds for Antihyperglycaemic Activity in Sucrose Challenged Streptozotocin STZ-Induced Diabetic Rats—

Induction of Diabetes in Rats:

Overnight starved male albino rats of Sprague Dawley strain were used and Diabetes was induced in the animals by single intraperitoneal injection of Streptozotocin at 60 mg/kg body weight dose prepared in 0.1M citrate buffer (pH 4.5). Fasting blood glucose level was measured by using a Glucometer (ACCU-CHEK II; Roche Diagnostics, USA) after 48 hours and animals showing blood glucose level above 140 mg/dl were considered as diabetic.

Grouping and Treatment:

The diabetic rats with fasting blood glucose values (baseline at 0 min) from 140 to 270 mg/dl were included in this study. All the diabetic animals were again divided into groups with five animals in each group. Animals of one group were regarded as the control group (orally administered 1% gum acacia) and the others were treated as the experimental groups. Rats in the experimental groups were orally administered suspension of the test compounds (100 mg/kg) prepared in 1.0% gum acacia. Animals of the control group were given an equal amount of 1.0% gum acacia. The standard antidiabetic drug Januvia was given to the animals at an oral dose of 50 mg/kg body weight. A sucrose load (2.5 g/kg) was given to each animal orally exactly after 30 min post administration of the test sample/vehicle. Blood glucose levels were checked at 1 h, 2 h, 3 h, 4 h, 5 h and 24 h post-administration of sucrose by glucometer. Food but not water was withheld from the cages during the course of experimentation. Percent hyperglycemic activity was determined by comparing the AUC (area under curve) of experimental groups with that of the vehicle treated control group.

In Vitro Activity Evaluation

Protein Tyrosine Phosphatase-1B Assay—

Protein tyrosine phosphatase-1B inhibitory activity of the compounds were evaluated at 10 µM concentration using colorimetric, non-radioactive PTP1B tyrosine phosphatase drug discovery kit BML-AK 822 from Enzo Life Sciences, USA. Components of the kit include human recombinant PTP1B enzyme, substrate (IR5 insulin receptor residues), biomol red (phosphate determining reagent), assay buffer, suramin (PTP1B inhibitor) and calibration standards. Assay was done according to the Kit manufacturers protocol, in brief the reaction was carried out in 96 well flat bottomed microtiter plate by the addition of assay buffer, solution of test compounds and diluted PTP1B enzyme. Enzyme reaction was initiated by addition of 50 µl of warmed 2× substrate then incubated the plate at 30° C. for 30 min. After incubation for 30 min. Reaction was terminated by addition of 25 µl of biomol red reagent and mixed thoroughly by repeated pipetting. Test compounds were dissolved in dimethyl sulfoxide (DMSO) and solution of 100 µM concentration was prepared of which 10 µl solution was added in each reaction well to achieve final concentration of 10 µM in reaction mixture. Volumes and dilution of other component were accordingly as instructed in the manual provided in the kit. PTP1B phosphatase acting on the phosphopeptide substrate and release phosphate. The detection of free phosphate released is based on classic Malachite green assay. After adding biomol red to reaction wells after 30 minutes of incubation as described earlier the plate was incubated for another 20 min to develop the colour. Absorbance was recorded at 620 nm. on a microplate reader. The percentage inhibition of PTP1b enzyme by test compounds was calculated based on activity in the control tube (without inhibitor) taking as 100% from three independent set of experiments.

To calculate the $IC_{50}$ value a series of dose response data ie. % inhibition of PTP 1B at different concentration of inhibitor is required. For the $IC_{50}$ value of compounds compound 5, compound 6% inhibition of at 5 different concentrations was evaluated using PTP1B tyrosine phosphatase drug discovery kit by the method as described above. Five different compound concentrations selected for $IC_{50}$ calculation were 0.3 µM, 1.0 µM, 3.0 µM, 5.0 µM, 10.0 µM and accordingly calculated the $IC_{50}$ value.

Statistical Analysis

Quantitative glucose tolerance of each animal was calculated by the area under the curve (AUC) method using Prism Software. The area under the curve of the control group and the experimental group was compared to determine the percent antihyperglycaemic activity. Statistical comparisons were performed by one-way analysis of variance (ANOVA), followed by Dunnett's multiple range test (DMRT). The results were considered statistically significant if the 'p' values were 0.05 or less. Results were expressed as mean±SEM.

Results—

TABLE 1

Effect of synthetic compounds (100 mg/kg) and standard drug Januvia (50 mg/kg) on the blood glucose levels at various time intervals.

| | | | | % Antihyperglycaemic activity | | | |
| | | | | STZ-S | | STZ | |
| S. No | Compound Code | Dose (mg/kg) | SLM | 0-5 h AUC | 0-24 h AUC | 0-5 h AUC | 0-24 h AUC |
|---|---|---|---|---|---|---|---|
| 1 | compound 5 | 100 | 35.8*** | 20.4** | 23.6*** | 23.1** | 18.2** |
| 2 | compound 6 | 100 | 23.5** | 29.7*** | 25.7*** | 18.9* | 20.1** |
| 3 | Januvia | 50 | 35.0*** | 21.8** | 23.8** | 28.2*** | 27.4*** |

Values are mean ± SEM, n = 5, *p < 0.05, p < 0.01 and *p < 0.001

TABLE 2

Effect of the synthetic compounds (at 100 mg/kg) and standard drug Januvia (at 50 mg/kg) on the blood glucose levels of the sucrose loaded normoglycaemic rats at various time intervals

| | Blood Glucose Profile (mg/dl) | | | | |
| Groups | 0 min | 30 min | 60 min | 90 min | 120 min |
|---|---|---|---|---|---|
| Sham Control | 66.2 ± 3.12 | 119.6 ± 5.3 | 120.8 ± 5.2 | 125.6 ± 9.22 | 126.6 ± 4.7 |
| compound 5 | 66.2 ± 3.05 | 107.4 ± 7.76 | 104.8 ± 5.12 | 108.3 ± 3.59 | 109.8 ± 7.86 |
| compound 6 | 66.2 ± 2.63 | 120.0 ± 7.30 | 111.2 ± 7.30 | 110.4 ± 4.73 | 107.4 ± 4.95 |
| januvia | 66.2 ± 0.73 | 114.0 ± 8.21 | 104.8 ± 5.70 | 112.0 ± 7.30 | 115.0 ± 7.67 |

Values are mean±S.E. of five rats in each group

TABLE 3

Effect of the synthetic compounds (at 100 mg/kg) and standard drug Januvia (at 50 mg/kg) on the blood glucose levels of the Sucrose challenged STZ induced diabetic rats at various time intervals.

| | Blood Glucose Profile (mg/dl) | | | | | | | | |
|---|---|---|---|---|---|---|---|---|---|
| | Pre treatment | | | | Post treatment | | | | |
| Groups | 0 min | 30 min | 60 min | 90 min | 120 min | 180 min | 240 min | 300 min | 1440 min |
| Sham Control | 222.6 ± 14.1 | 501.3 ± 12.3 | 598.1 ± 1.83 | 592.8 ± 4.23 | 556.5 ± 12.4 | 524.1 ± 14.9 | 498.8 ± 15.2 | 469.8 ± 16.4 | 444.0 ± 11.3 |
| compound 5 | 222.3 ± 9.39 | 515.6 ± 15.5 | 528.6 ± 14.4 | 506.5 ± 14.0 | 459.6 ± 11.2 | 402.1 ± 5.58 | 332.5 ± 15.6 | 284.3 ± 16.9 | 411.1 ± 13.6 |
| compound 6 | 222.6 ± 6.55 | 442.1 ± 18.2 | 520.0 ± 10.3 | 464.0 ± 14.4 | 399.3 ± 14.0 | 334.0 ± 13.4 | 301.6 ± 18.8 | 277.0 ± 10.1 | 405.0 ± 17.6 |
| Januvia | 222.3 ± 16.2 | 455.0 ± 14.2 | 519.8 ± 16.0 | 469.3 ± 9.40 | 439.3 ± 14.2 | 377.6 ± 10.1 | 359.5 ± 10.1 | 337.6 ± 8.18 | 394.6 ± 8.34 |

TABLE 4

Effect of the synthetic compounds (at 100 mg/kg) and standard drug Januvia (at 50 mg/kg) on the blood glucose levels of the low dosed STZ induced diabetic rats at various time intervals.

| | Blood Glucose Profile (mg/dl) | | | | | | | | |
|---|---|---|---|---|---|---|---|---|---|
| | Pre treatment | | | | Post treatment | | | | |
| Groups | 0 min | 30 min | 60 min | 90 min | 120 min | 180 min | 240 min | 300 min | 1440 min |
| Sham Control | 343.4 ± 3.15 | 440.2 ± 12.9 | 547.4 ± 14.4 | 567.8 ± 10.4 | 580.0 ± 9.25 | 545.2 ± 8.35 | 517.0 ± 12.6 | 515.8 ± 16.2 | 498.6 ± 26.2 |
| compound 5 | 346.6 ± 6.19 | 434.2 ± 12.4 | 481.2 ± 11.8 | 447.0 ± 8.16 | 434.8 ± 11.7 | 385.6 ± 5.8 | 353.6 ± 16.4 | 362.4 ± 17.6 | 483.0 ± 3.95 |
| compound 6 | 344.0 ± 3.91 | 444.6 ± 16.6 | 492.0 ± 13.6 | 490.2 ± 11.2 | 474.8 ± 15.0 | 426.0 ± 16.0 | 385.8 ± 15.6 | 355 ± 14.3 | 442.4 ± 9.64 |
| Januvia | 341.4 ± 3.53 | 445.8 ± 13.0 | 497.4 ± 11.2 | 473.4 ± 11.2 | 392.0 ± 11.8 | 348.2 ± 16.7 | 300.4 ± 14.7 | 255.0 ± 16.9 | 484.4 ± 10.7 |

TABLE 5

Effect of the synthetic compounds as PTP-1B inhibitor.

| Compound number | % Inhibition |
|---|---|
| 1 | 9.20 |
| 2 | 8.00 |
| 3 | 8.43 |
| 4 | 16.4 |
| 5 | 83.8 |
| 6 | 76.9 |
| 7 | 12.7 |
| 8 | 14.6 |
| 9 | 10.7 |
| 10 | 1.52 |
| 11 | 18.8 |
| 12 | 26.4 |
| Standard Suramin | 60.2 (IC$_{50}$ 9.5 µM) |

TABLE 6

Inhibitory activity of compounds 5 and 6 at different concentration and IC$_{50}$ value for PTP1B.

| S. No. | Compd Code | % Inhibition at different Inhibitor concentration | | | | | IC$_{50}$ (µM) |
|---|---|---|---|---|---|---|---|
| | | 10 µM | 5 µM | 3 µM | 1 µM | 0.3 µM | |
| 1 | compound 5 | 67.8 | 36.67 | 24.10 | 13.23 | 3.89 | 7.12 |
| 2 | compound 6 | 62.28 | 28.76 | 16.25 | 11.23 | 0.50 | 8.12 |

Results—

The effect exerted by compound 5 and 6 at the dose level of 100 mg/kg is comparable with the standard drug Januvia at the dose level of 50 mg/kg.

Effect of Synthetic Compounds on Sucrose Loaded Normoglycemic Rats:

Table 1, 2 and FIG. 1 shows the effect of compound 5 and 6 (100 mg/kg b.w.) and Januvia (50 mg/kg b.w.) on sucrose loaded normoglycemic rats. It is evident from the results that compound 5 and 6 show significant improvement in glucose tolerance. The fasting blood glucose levels (mean±SEM) of the test compounds, standard drug Januvia and control groups were 66.2±3.05, 66.2±2.63, 66.3±3.12 and 66.0±0.78 mg/dl (Table 2) respectively. Two hours after administration of sucrose, the mean blood glucose concentrations of the test compound treated group (109.8±7.86 and 107.4±4.95 mg/dl) and the Januvia treated group (115.0±7.67 mg/dl), were significantly lower ($p<0.05$, $p<0.01$ and $p<0.001$) than that of the control group treated with 1% gum acacia (126.6±4.7 mg/dl). The decrease in the blood glucose level at 2 hrs in the test group compared with that of the control was 35.8% and 23.5% whereas the decrease in the Januvia treated group was 35.0%.

Figure 2:
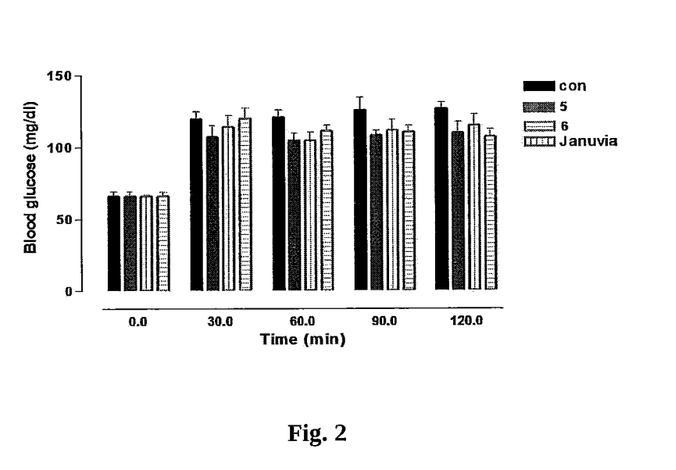
FIG. 2 illustrates the effect of the synthetic compounds and standard drug Januvia (at 50 mg/kg) on the blood glucose levels of sucrose loaded normoglycaemic rats at various time intervals.

Effect of Synthetic Compounds on Sucrose Challenged Streptozotocin-Induced Diabetic Rats:

Table 1, 3 and FIG. 2 represent the average antihyperglycaemic activity profile of compound 5 and 6 and standard drug Januvia in the sucrose challenged streptozotocin-induced diabetic rats. The fasting blood glucose levels (mean±SEM) of the test compounds, standard drug and control groups were 222.3±9.39, 222.6±6.55, 222.3±16.2 and 222.6±14.1 mg/dl (Table 3) respectively. Five hours after administration of sucrose, the mean blood glucose concentrations of the test compound treated group (284.3±16.9 and 277.0±10.1 mg/dl) and the Januvia treated group (337.6±8.18 mg/dl), were significantly lower ($p<0.01$, $p<0.001$ and $p<0.001$) than that of the control group treated with 1% gum acacia (469.8±16.4 mg/dl) and after 24 hours the mean blood glucose concentration of the test compounds are 411.1±13.6, 405.0±17.6 mg/dl and standard drug Januvia treated group 394.6±8.34 than that of the control group 444.0±11.3 mg/dl. It is evident from the result that compound 5 and 6 caused a significant decline of 20.4% ($p<0.01$), 29.7 and 23.6 and 25.7% ($p<0.001$) in the hyperglycaemia of the diabetic rats post sucrose-load after 5 hour interval, and respectively. The standard drug Januvia at the same dose level of 50 mg/kg showed a blood glucose lowering effect of 21.8 and 23.8% ($p<0.01$) after 5 h and 24 intervals.

Figure 3:
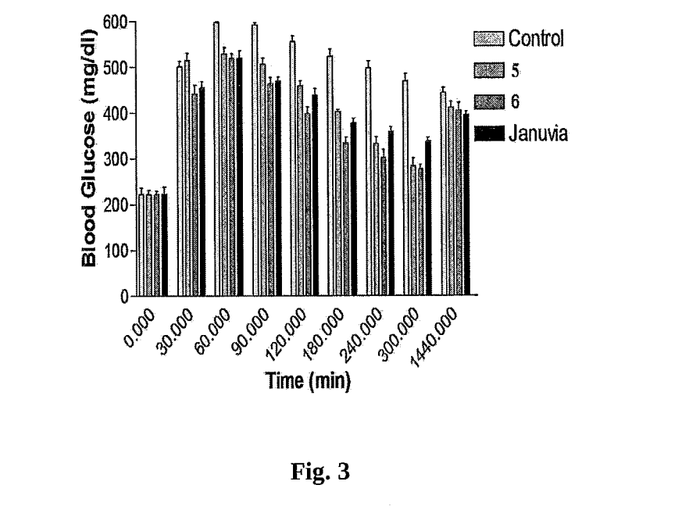
FIG. 3 illustrated the effect of the synthetic compounds and standard drug Januvia (at 50 mg/kg) on the blood glucose levels of the sucrose challenged STZ induced diabetic rats at various time intervals.
Figure 4:
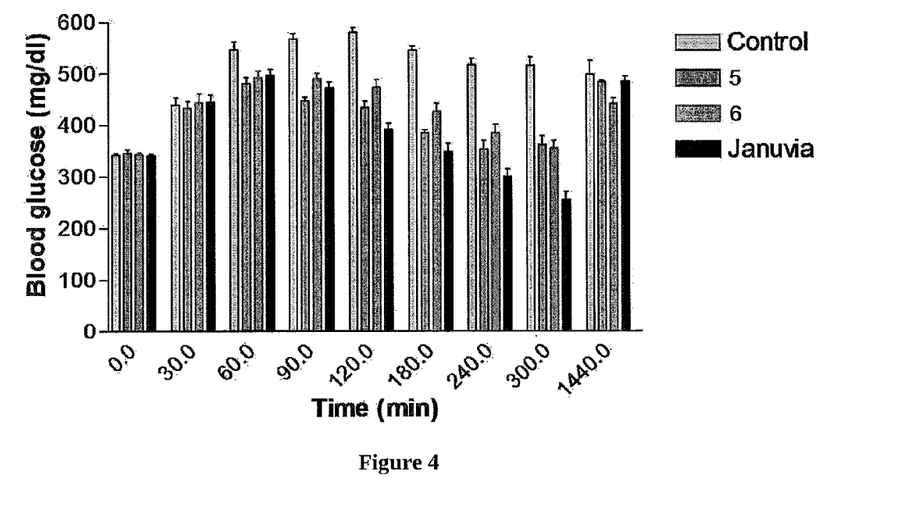
FIG. 4 illustrates the effect of the synthetic compounds and standard drug Januvia (at 50 mg/kg) on the blood glucose levels of the Low dosed STZ induced diabetic rats at various time intervals.

Effect of Synthetic Compounds on Low Dosed Streptozotocin-Induced Diabetic Rats:

The results obtained from the variance analysis showed in Tables 1, 4 and FIG. 3, depict the antihyperglycaemic activity profile of experimental groups. When these compound 5 and 6 were evaluated in the low dosed streptozotocin induced diabetic rats, they caused significant lowering in the hyperglycaemia of the diabetic rats. Table 4 and FIG. 3 represent the average antihyperglycaemic activity profile of compound 5 and 6 and standard drug Januvia in the low dosed streptozotocin-induced diabetic rats. The fasting blood glucose levels (mean±SEM) of the test, standard drug and control groups were 346.6±6.19, 344.0±3.91, 341.4±3.53 and 343.4±3.15 mg/dl (Table 4) respectively. After Six hours the mean blood glucose concentrations of the test compound treated group (362.4±17.6 and 355.0±14.3 mg/dl) and the Januvia treated group (255.0±16.9 mg/dl), were significantly lower ($p<0.01$, $p<0.001$ and $p<0.001$) than that of the control group treated with 1% gum acacia (515.8±16.2 mg/dl) and after 24 hours the mean blood glucose concentration of the test compounds are 483.0±3.95, 442.4±9.64 mg/dl and standard drug Januvia treated group 484.4±10.7 than that of the control group 498.6±2.62 mg/dl. It is evident from the result that compound 5 and 6 caused a significant decline of 23.1% ($p<0.05$), 18.9 and 18.2 and 20.1% ($p<0.01$) in the hyperglycaemia of the diabetic rats post sucrose-load after 5 hour interval and respectively. The standard drug Januvia at the dose level of 50 mg/kg showed a blood glucose lowering effect of 28.2 and 27.4% ($p<0.001$) after 5 h and 24 intervals.

Effect of Synthetic Compounds on PTP-1B Inhibition—

A series of synthetic 4,5-dihydro-2H-benzo[e]indazole compounds were evaluated against PTP1B using colorimetric, non-radioactive PTP1B tyrosine phosphatase drug discovery kit BML-AK 822. The study showed that compound 1-4 and compound 7-12 did not show any significant activity. It is evident from the activity profile (Table 5) that compound 5 and 6 were found to show good PTP-1B inhibition with $IC_{50}$ of 7-8 µM.

Advantages of the present invention are the synthesis and identification of a novel series of 4,5-dihydro-2H-benzo[e] indazole compounds prepared through innovative route under mild reaction conditions and their useful anti-hyperglycemic activity in both in vitro (PTP-1B inhibitors) and in vivo (SLM, STZ, STZ-S animal models). These compounds hold therapeutic potential for the treatment of diabetes and related metabolic disorders.

We claim:

1. A compound of Formula I or pharmaceutically acceptable salt thereof

Formula I (a) wherein $R^1$ is independently selected from the groups consisting of optionally substituted aryl, optionally substituted heteroaryl;

(b) wherein $R^2$, $R^3$ are independently selected from the groups consisting of hydrogen, optionally substituted alkyl, optionally substituted aryl, optionally substituted heteroaryl, optionally substituted cycloalkenyl;

(c) wherein $R^4$ is independently selected from the groups consisting of optionally substituted alkylthio, optionally substituted alkylsulfonyl, optionally substituted amines;

(d) wherein R is independently selected from the groups consisting of hydrogen, optionally substituted alkyl, optionally substituted alkenyl, optionally substituted aryl groups;

(e) wherein Y is selected from the groups consisting of one methylene group, two methylene groups, or optionally substituted methylene group.

2. The compound as claimed in claim 1 wherein the compound is:

Methyl 6-(4-bromophenyl)-8-(methylthio)-2-phenyl-4,5-dihydro-2H-benzo[e]indazole-9-carboxylate;

Methyl 6-(4-chlorophenyl)-8-(methylthio)-2-phenyl-4,5-dihydro-2H-benzo[e]indazole-9-carboxylate;

Methyl 6-(4-methoxyphenyl)-8-(methylthio)-2-phenyl-4,5-dihydro-2H-benzo[e]indazole-9-carboxylate;

Methyl 8-(methylthio)-2,6-diphenyl-4,5-dihydro-2H-benzo[e]indazole-9- carboxylate;

Methyl 8-(methylthio)-2-phenyl-6-p-tolyl-4,5-dihydro-2H-benzo[e]indazole-9-carboxylate;

Methyl 8-(methylthio)-6-(naphthalen-1-yl)-2-phenyl-4,5-dihydro-2H-benzo[e]indazole-9-carboxylate;

Methyl 8-(methylthio)-2-phenyl-6-(thiophen-2-yl)-4,5-dihydro-2H-benzo[e]indazole-9-carboxylate;

Methyl 6-(4-fluorophenyl)-8-(methylthio)-2-phenyl-4,5-dihydro-2H-benzo[e]indazole-9-carboxylate;

Methyl 8-(methylthio)-2-phenyl-6-(pyren-1-yl)-4,5-dihydro-2H-benzo[e]indazole-9-carboxylate;

Methyl 6-(4-fluorophenyl)-8-(methylsulfonyl)-2-phenyl-4,5-dihydro-2H-benzo[e]indazole-9-carboxylate;

Methyl 8-(methylsulfonyl)-6-(naphthalen-1-yl)-2-phenyl-4,5-dihydro-2H-benzo[e]indazole-9-carboxylate;

Methyl 8-(methylsulfonyl)-2-phenyl-6-(p-tolyl)-4,5-dihydro-2H-benzo[e]indazole-9-carboxylate; or Methyl 5-(methylthio)-7-(naphthalen-2-yl)-2-phenyl-2,8-dihydroindeno[2,1-c]pyrazole-4-carboxylate.

3. The compound as claimed in claim 1, for use in a method of treating diabetes and related disorders.

4. A process for synthesis of the compound of Formula I:

Formula I (a) wherein R1 is independently selected from the groups consisting of optionally substituted aryl, optionally substituted heteroaryl;
(b) wherein R2, R3 are independently selected from the groups consisting of hydrogen, optionally substituted alkyl, optionally substituted aryl, optionally substituted heteroaryl, optionally substituted cycloalkenyl;
(c) wherein R4 is independently selected from the groups consisting of optionally substituted alkylthio, optionally substituted alkylsulfonyl, optionally substituted amines;
(d) wherein R is independently selected from the groups consisting of hydrogen, optionally substituted alkyl, optionally substituted alkenyl, optionally substituted aryl groups;
(e) wherein Y is selected from the groups consisting of one methylene group, two methylene groups, or optionally substituted methylene group, which comprises:
(a) reacting 2H-pyran-2-ones with a cyclic ketone in presence of an alkali base for a period upto 24 hours at a temperature ranging between 0 to 50 degree centigrade;
(b) pouring the reaction mixture to an ice cold water and neutralizing with an acid;
(c) purifying the product by chromatographic method,
(d) optionally, reacting the compound obtained in above step with m-chloroperbenzoic acid in dichloromethane at a temperature ranging between 25 to 28 degree C. for a period ranging between 1-2 hrs, treating the reaction mixture with sodium bicarbonate solution to obtain the desired compound.

5. The process as claimed in claim 4, wherein the cyclic ketone is a substituted or unsubstituted cyclic ketone, including 2-phenyl-6,7-dihydro-2H-indazol-4(5H)-one.

6. The process as claimed in claim 4, wherein the organic solvent is selected from the group consisting of acetone, N,N-dimethyl formamide, N,N-dimethyl acetamide, dimethyl sulfoxide, benzene, toluene, xylene, chlorobenzene and tetrahydrofuran.

7. The process as claimed in claim 4, wherein the base is selected from a group consisting of NaOH, KOH, NaH, t-BuOK, $K_2CO_3$, and NaOEt.

8. The process as claimed in claim 4, wherein the neutralization of the resultant compounds is effected by acidifying the reaction mixture with dilute hydrochloric acid, sulfuric acid and acetic acid.

9. A pharmaceutical composition comprising an effective amount of compound of Formula I:

Formula I (a) wherein R1 is independently selected from the groups consisting of optionally substituted aryl, optionally substituted heteroaryl;
(b) wherein R2, R3 are independently selected from the groups consisting of hydrogen, optionally substituted alkyl, optionally substituted aryl, optionally substituted heteroaryl, optionally substituted cycloalkenyl;
(c) wherein R4 is independently selected from the groups consisting of optionally substituted alkylthio, optionally substituted alkylsulfonyl, optionally substituted amines;
(d) wherein R is independently selected from the groups consisting of hydrogen, optionally substituted alkyl, optionally substituted alkenyl, optionally substituted aryl groups;
(e) wherein Y is selected from the groups consisting of one methylene group, two methylene groups, or optionally substituted methylene group optionally along with pharmaceutically acceptable, excipients, carrier/s, lubricants, and diluents.

10. The pharmaceutical composition as claimed in claim 9, wherein the effective amount of the compound is from 10 mg to 500 mg.

11. A method of treating diabetes in a subject, comprising the step of administering to the subject suffering from diabetes, a pharmaceutical composition comprising an effective amount of a compound of Formula I:

Formula I (a) wherein R1 is independently selected from the groups consisting of optionally substituted aryl, optionally substituted heteroaryl;
(b) wherein R2, R3 are independently selected from the groups consisting of hydrogen, optionally substituted alkyl, optionally substituted aryl, optionally substituted heteroaryl, optionally substituted cycloalkenyl;
(c) wherein R4 is independently selected from the groups consisting of optionally substituted alkylthio, optionally substituted alkylsulfonyl, optionally substituted amines;
(d) wherein R is independently selected from the groups consisting of hydrogen, optionally substituted alkyl, optionally substituted alkenyl, optionally substituted aryl groups;
(e) wherein Y is selected from the groups consisting of one methylene group, two methylene groups, or optionally substituted methylene group optionally along with pharmaceutically acceptable, excipients, carrier/s, lubricants, diluents.

12. A compound as claimed in claim 1, for use in a method of treating hyperglycemia.

13. The method of treating diabetes as claimed in claim 11, wherein the compound is Methyl 8-(methylthio)-2-phenyl-6-p-tolyl-4,5-dihydro-2H-benzo[e]indazole-9-carboxylate.

14. The method of treating diabetes as claimed in claim 11, wherein the compound is Methyl 8-(methylthio)-6-(naphthalen-1-yl)-2-phenyl-4,5-dihydro-2H-benzo[e]indazole-9-carboxylate.

* * * * *